United States Patent
Ho et al.

(10) Patent No.: US 9,994,679 B2
(45) Date of Patent: Jun. 12, 2018

(54) POLYMERIZATION PROCESS OF POLYARYLENE SULFIDE

(71) Applicant: INDUSTRIAL TECHNOLOGY RESEARCH INSTITUTE, Hsinchu (TW)

(72) Inventors: Po-Hsien Ho, Taipei (TW);
Chih-Hsiang Lin, Taipei (TW);
Meng-Hsin Chen, Pingtung County (TW); Cheng-Hsing Fan, Tainan (TW);
Hsin-Ching Kao, Hsinchu (TW);
Yih-Her Chang, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 22 days.

(21) Appl. No.: 15/381,684

(22) Filed: Dec. 16, 2016

(65) Prior Publication Data

US 2017/0204225 A1  Jul. 20, 2017

Related U.S. Application Data

(60) Provisional application No. 62/277,091, filed on Jan. 11, 2016.

(51) Int. Cl.
*C08G 75/00* (2006.01)
*C08G 75/025* (2016.01)
(Continued)

(52) U.S. Cl.
CPC .......... *C08G 75/025* (2013.01); *C07C 319/14* (2013.01); *C07C 381/12* (2013.01);
(Continued)

(58) Field of Classification Search
CPC .... C07F 7/0801; C07F 7/0832; C07F 7/0827; C08G 75/00; C07B 51/00; C07D 209/12
See application file for complete search history.

(56) References Cited

U.S. PATENT DOCUMENTS

2,739,991 A  3/1956 Hervert
2,843,643 A  7/1958 Gleim
(Continued)

FOREIGN PATENT DOCUMENTS

EP  3034542 A1  6/2016
EP  3042924 A1  7/2016
(Continued)

OTHER PUBLICATIONS

European Office Action issued in European Application No. 17150823.7 dated Sep. 25, 2017.
(Continued)

*Primary Examiner* — Shane Fang
(74) *Attorney, Agent, or Firm* — Birch, Stewart, Kolasch & Birch, LLP

(57) ABSTRACT

A method for preparing a polyarylene sulfide includes reacting a methyl 4-(arylthio)aryl sulfoxide compound with sulfuric acid, methanesulfonic acid, benzenesulfonic acid, p-toluenesulfonic acid or trifluoromethanesulfonic acid to obtain a polysulfonium intermediate; and demethylating the polysulfonium intermediate to obtain a polyarylene sulfide, wherein the polysulfonium intermediate is demethylated with aqueous HCl, HBr, or HI.

10 Claims, 2 Drawing Sheets

DSC spectrum of PPS

(51) Int. Cl.
  C08G 75/0227     (2016.01)
  C08G 75/02       (2016.01)
  C08G 75/0204     (2016.01)
  C07C 319/14      (2006.01)
  C07C 381/12      (2006.01)
(52) U.S. Cl.
  CPC ......... *C08G 75/02* (2013.01); *C08G 75/0204* (2013.01); *C08G 75/0227* (2013.01)

(56) References Cited

U.S. PATENT DOCUMENTS

| | | | |
|---|---|---|---|
| 3,354,129 | A | 11/1967 | Edmonds, Jr. et al. |
| 4,124,646 | A | 11/1978 | Kawamura et al. |
| 4,786,713 | A | 11/1988 | Rule et al. |
| 6,111,143 | A | 8/2000 | Park et al. |
| 8,445,629 | B2 | 5/2013 | Hinokimori et al. |
| 8,492,502 | B2 | 7/2013 | Lee et al. |
| 8,759,478 | B2 | 6/2014 | Shin et al. |
| 8,957,182 | B2 | 2/2015 | Lee et al. |
| 2004/0013926 | A1 | 1/2004 | Akita et al. |
| 2014/0128568 | A1 | 5/2014 | Hinokimori |
| 2016/0200874 | A1 | 7/2016 | Watanabe et al. |

FOREIGN PATENT DOCUMENTS

| | | |
|---|---|---|
| JP | 1-78993 U | 5/1989 |
| JP | 5-178993 A | 7/1993 |
| JP | 7-304872 A | 11/1995 |
| JP | 9-48854 A | 2/1997 |
| JP | 10-182823 A | 7/1998 |
| JP | 10-182825 A | 7/1998 |
| JP | 2988827 B2 | 12/1999 |
| KR | 10-2007-0036776 A | 4/2007 |
| TW | 201512249 A | 4/2015 |
| WO | WO 2015/033938 A1 | 3/2015 |
| WO | WO 2015/033936 A1 | 12/2015 |

OTHER PUBLICATIONS

Extended European Search Report issued in European Application No. 17150788.2 dated Apr. 21, 2017.
Extended European Search Report issued in European Application No. 17150823.7 dated Apr. 18, 2017.
Extended European Search Report issued in European Application No. 17150883.1 dated Apr. 10, 2017.
Extended European Search Report issued in European Application No. 17150910.2 dated Mar. 28, 2017.
Extended European Search Report issued in European Application No. 17150978.9 dated Mar. 28, 2017.
Gabler et al., "Neue Polyphenylensulfone Reaktionen an Festen Polymeren," Chimia International Journal for Chemistry, vol. 28, No. 9, Sep. 1974, pp. 567-575, with an English abstract.
Hartke et al., "Reaction of Thioanisol with Antimony Pentachloride," Arch. Pharm., vol. 315, No. 2, 1982, pp. 153-156, with an English abstract.
Ogawa et al., "Development of New Synthetic Procedure of Poly(phenylene sulfide)," Abstracts of The 37th Symposium on Main Group Element Chemistry, vol. 37, 2010, pp. 301-302, with an English abstract.
Schultz et al., "New Catalysts for the Oxidation of Sulfides to Sulfones with Hydrogen Peroxide," The Journal of Organic Chemistry, vol. 28, Iss.4, Apr. 1963, pp. 1140-1142.
Taiwanese Notice of Allowance and Search Report issued in Taiwanese Application No. 105143834 dated Sep. 6, 2017.
Taiwanese Notice of Allowance issued in Taiwanese Application No. 105143831 dated Oct. 3, 2017.
Taiwanese Office Action and Search Report issued in Taiwanese Application No. 105142423 dated Apr. 13, 2017.
Taiwanese Office Action and Search Report issued in Taiwanese Application No. 105142916 dated Jun. 12, 2017.
Taiwanese Office Action and Search Report issued in Taiwanese Application No. 105143831 dated Jul. 3, 2017.
Tsuchida et al., "Photochemical recycling of polyarylene sulfide," Chemical Communications, No. 17, Sep. 7, 1996, pp. 2091-2092.
Tsuchida et al., "Synthesis of high molecular weight poly(phenylene sulfide) by oxidative polymerization via poly(sulfonium cation) from methyl phenyl sulfoxide," Macromolecules, vol. 26, No. 26, Dec. 20, 1993 (abstract published Nov. 15, 1993), pp. 7144-7148.
Tsuchida et al., "Synthesis of Poly(phenylene sulfide) by $O_2$ Oxidative Polymerization of Methyl Phenyl Sulfide," Macromolecules, vol. 27, No. 4, Feb. 14, 1994 pp. 1057-1060.
U.S. Office Action issued in U.S. Appl. No. 15/388,215 dated Sep. 8, 2017.
U.S. Office Action issued in U.S. Appl. No. 15/389,785 dated Sep. 29, 2017.
Yamamoto et al., "Aryl sulfide bond formation using the sulfoxide-acid system for synthesis of PPS via poly(sulfonium cation) as a precursor," Journal of The American Chemical Society, vol. 115, No. 13, Jun. 1993, pp. 5819-5820.
Yamamoto et al., "Oxidative Coupling of Methyl Phenyl Sulfide via Sulfonium Formation Using an Oxovanadium Complex," The Journal of Organic Chemistry, vol. 61, No. 6, Mar. 22, 1996, pp. 1912-1913.
Yamamoto et al., "Synthesis of poly(sulfonium cation) by oxidative polymerization of aryl alkyl sulfides," The Journal of Organic Chemistry, vol. 60, No. 2, 1995, pp. 452-453.
Haryono, A., et al, "Synthesis and Nucleophilic Dealkylation of Poly[alkyl-(4-(phenylthio)phenyl)sulfonium trifluoromethanesulfonate]s," Macromolecules, 1998, vol. 31, pp. 1202-1207.
Ho, et al., U.S. Appl. No. 15/388,215, filed Dec. 22, 2016.
Ho, et al., U.S. Appl. No. 15/389,711, filed Dec. 23, 2016.
Ho, et al., U.S. Appl. No. 15/389,785, filed Dec. 23, 2016.
Ho, et al., U.S. Appl. No. 15/939,913, filed Dec. 29, 2016.
Miyatake, K., et al, "Polymerization of Methyl Phenyl Sulfoxide under Acidic Conditions: Synthesis and X-ray Structure Analysis of a Phenylene Sulfonium Polymer," Macromolecules, 2001, vol. 34, pp. 1172-1179.
Miyatake, K., et al, "Synthesis and Proton Conductivity of Highly Sulfonated Poly(thiophenylene)," Macromolecules, 1997, vol. 30, pp. 2941-2946.
Tsuchida, E., et al, "First Phenylene Polymers Linked by Sulfonium Groups," Angew. Chem. Int. Engl., 1996, vol. 35, No. 23/24, pp. 2843-2845.
Yamamoto, K., et al, "Sulfide Bond Formation for the Synthesis of Poly(thioarylene) through Oxidation of Sulfur Chloride with Aromatics," Macromolecules, 1994, vol. 27, pp. 4312-4317.
Ho, et al., U.S. Appl. No. 15/393,913, filed Dec. 29, 2016.

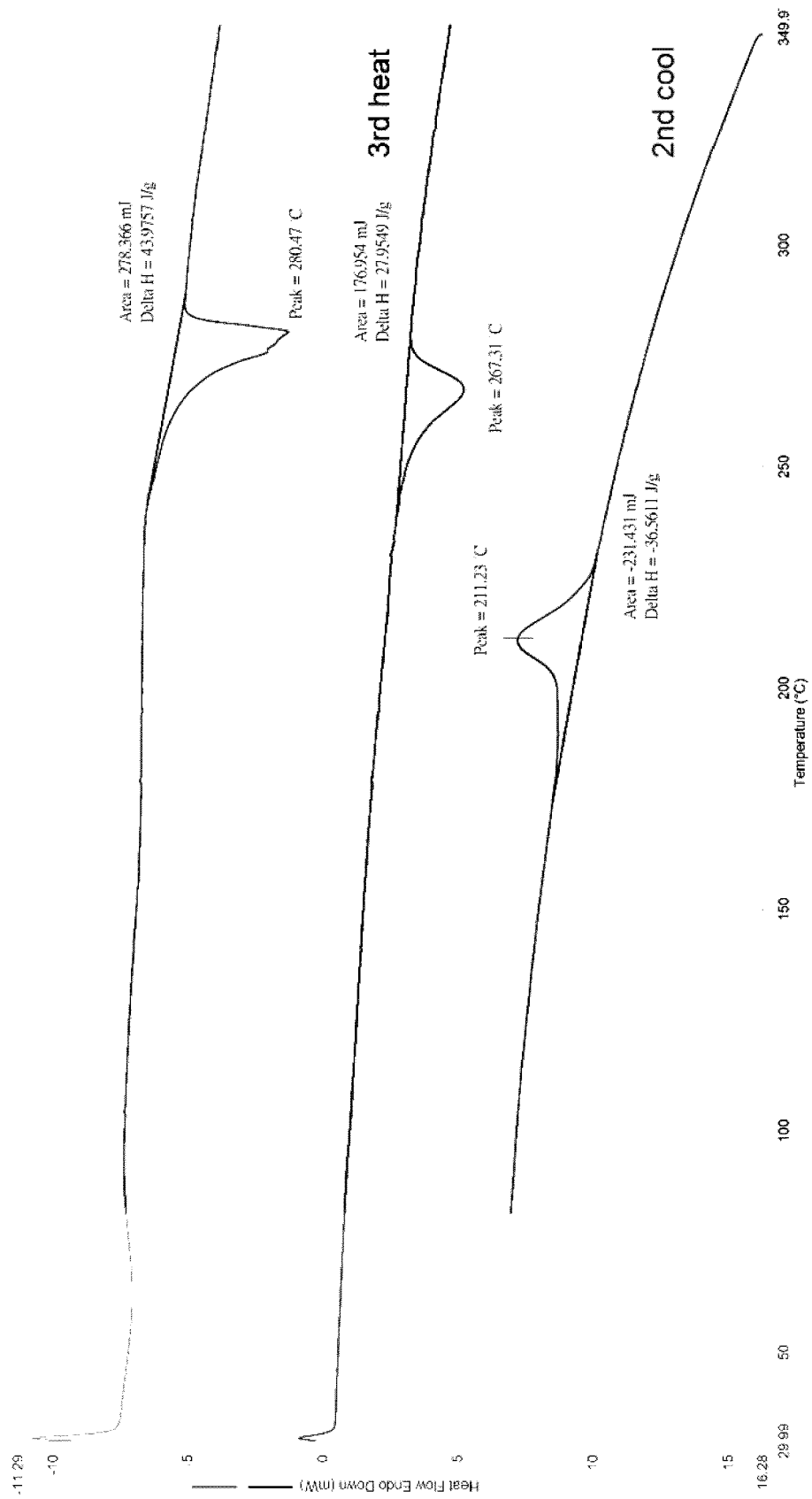
Fig1. DSC spectrum of PPS

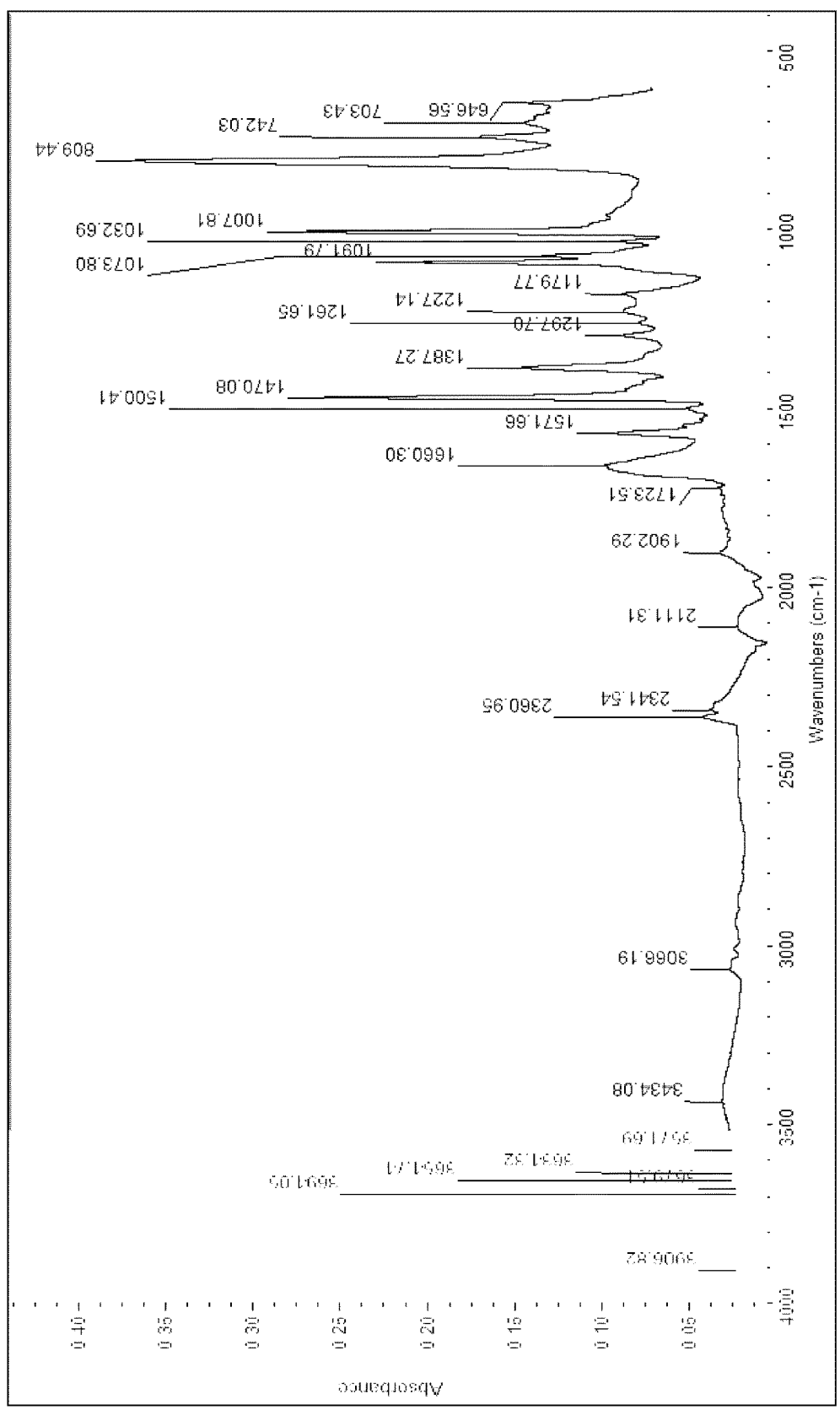
Fig2. IR spectrum of PPS

POLYMERIZATION PROCESS OF POLYARYLENE SULFIDE

CROSS REFERENCE TO RELATED APPLICATIONS

This non-provisional application claims the benefit under 35 U.S.C. § 119(e) to U.S. Provisional Application No. 62/277,091, filed on Jan. 11, 2016, which is hereby expressly incorporated by reference into the present application.

BACKGROUND

1. Technical Field

The technical field relates to a method for preparing polyarylene sulfide.

2. Description of the Background Art

Polyarylene sulfide (PAS), specifically polyphenylene sulfide (PPS), is a material with good mechanical properties and excellent thermal and chemical resistance compared to metals of the electronic and automobile industry due to its low density. PAS is also useful in spinning fibers of filters, connectors, coating material, and electronic components. Conventionally, the preparation of PAS is formed by reacting p-dichlorobenzene and sodium sulfide as monomers. A massive byproduct of alkali metal halide resides in the PAS resin, so the PAS resin needs some purification steps. However, purification by removal of the salty waste increases the production cost, degrades the quality, and decreases the efficiency of the production of PAS resin.

JP 07-304872 A discloses the preparation of a polysulfonium intermediate by reacting methyl 4-(phenylthio)phenyl sulfoxide in trifluoromethanesulfonic acid and then demethylating the polysulfonium intermediate with pyridine to obtain a neutral PAS resin with pyridinium salt as a byproduct. This reaction scheme is illustrated below.

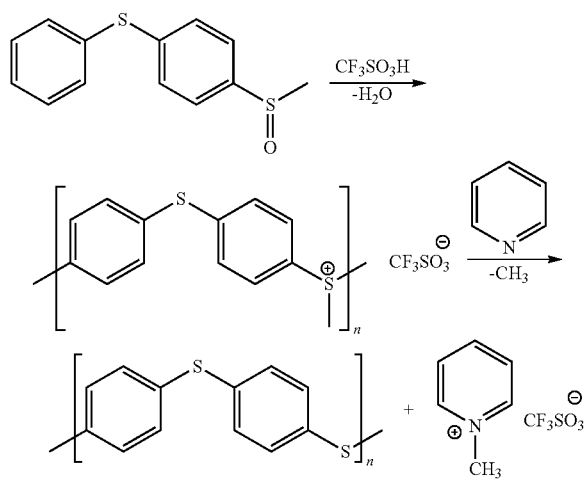

However, a salty waste byproduct such as pyridinium salt is disadvantageous. Specifically, a salty waste byproduct results in increased cost due to the additional steps needed to purify the PAS resin. In addition, the salty waste byproduct is not environmentally friendly. Therefore, an industry-wide need exists for a method of preparing a polyarylene sulfide without a salty byproduct.

SUMMARY

The disclosed embodiment relates to a method of preparing PAS without salty waste.

One embodiment is directed to a method for preparing a polyarylene sulfide of formula (1), comprising reacting methyl 4-(arylthio)aryl sulfoxide according to the following formula (2) with sulfuric acid, methanesulfonic acid, benzenesulfonic acid, p-toluenesulfonic acid, or trifluoromethanesulfonic acid to obtain a nolvsulfonium intermediate:

wherein $Ar_1$ and $Ar_2$ are aryl groups that may be the same or different and n is an integer of 2 to 1000; and demethylating the polysulfonium intermediate to obtain a polyarylene sulfide, wherein the polysulfonium intermediate is demethylated with aqueous HCl, HBr, or HI.

Further scope of applicability of the disclosed embodiment will become apparent from the detailed description given hereinafter. However, it should be understood that the detailed description and specific examples, while indicating alternative embodiments of the disclosed embodiment, are given by way of illustration only, since various changes and modifications within the spirit and scope of the disclosed embodiment will become apparent to one of ordinary skill in the art from this detailed description.

BRIEF DESCRIPTION OF THE DRAWINGS

The disclosed embodiment will become more fully understood from the detailed description given below and the accompanying drawings that are given by way of illustration only and are thus not limitative of the disclosed embodiment.

FIG. 1 is a differential scanning calorimetry (DSC) spectrum of the polyphenylene sulfide produced in the examples.

FIG. 2 is an infrared (IR) spectrum of the polyphenylene sulfide produced in the examples.

DETAILED DESCRIPTION OF THE DISCLOSED EMBODIMENT

In the following detailed description, for purposes of explanation, numerous specific details are set forth in order to provide a thorough understanding of the disclosed embodiments. It will be apparent, however, that one or more embodiments may be practiced without these specific details. The inventive concept may be embodied in various forms without being limited to the exemplary embodiments set forth herein.

The disclosed embodiment is directed to a method for preparing a polyarylene sulfide.

The polyarylene sulfide has the following structure according to formula (1):

wherein $Ar_1$ and $Ar_2$ are aryl groups that may be the same or different and may be a phenyl group, a biphenyl group, a naphthyl group, a thienyl group, a tolyl group, a xylyl group, an indolyl group, a tetrahydronaphthyl group, a phenanthrenyl group, a biphenylenyl group, an indenyl group, an anthracenyl group, or a fluorenyl group. The aryl group may have a single ring, two fused rings, or three fused rings. For example, the aryl group may be a phenyl group. As such, the polyarylene sulfide may be polyphenylene sulfide.

n is an integer ranging from 1 to 1000 or from 2 to 1000.

The first step for preparing the polyarylene sulfide comprises reacting a methyl 4-(arylthio)arylsulfoxide compound with an acid. The methyl 4-(arylthio)aryl sulfoxide compound has the following structure according to formula (2):

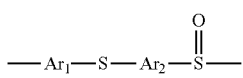

(2)

wherein $Ar_1$ and $Ar_2$ are aryl groups that may be the same or different and may be a phenyl group, a biphenyl group, a naphthyl group, a thienyl group, a tolyl group, a xylyl group, an indolyl group, a tetrahydronaphthyl group, a phenanthrenyl group, a biphenylenyl group, an indenyl group, an anthracenyl group, or a fluorenyl group. The aryl group may have a single ring, two fused rings, or three fused rings. For example, the aryl group may be a phenyl group. The methyl 4-(arylthio)aryl sulfoxide may be methyl 4-(phenylthio)phenyl sulfoxide.

The acid may be sulfuric acid, methanesulfonic acid, benzenesulfonic acid, p-toluenesulfonic acid, or trifluoromethanesulfonic acid.

Weight moderate methyl-4-(phenylthio)phenyl sulfoxide, and sulfonic acid as solvent may be added inside the reaction between about 0 and 25° C. in about 0.5 atm to 1.5 atm. The reaction may be continuously kept about 0.5 hour to 1.5 hours between about 0° C. and 25° C.; then the temperature may be raised to about 20° C. to 50° C. (for example, about 25° C.) and the reaction may keep proceeding for about 4 hours to 72 hours (for example, about 10 hours to 30 hours). After finishing, the white solid may be recrystallized in ethanol. As one embodiment, methyl 4-(arylthio)aryl sulfoxide and the acid may be reacted at about 0° C. for about 1 hour, and then, the temperature of the reaction may be raised to about 25° C. for about 20 hours.

When the methyl 4-(arylthio)aryl sulfoxide is reacted with an acid, a polysulfonium intermediate is obtained. The polysulfonium intermediate may have the following structure according to formula (3):

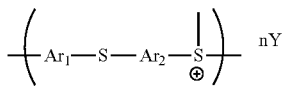

(3)

wherein $Ar_1$ and $Ar_2$ are aryl groups that may be the same or different and may be a phenyl group, a biphenyl group, a naphthyl group, a thienyl group, a tolyl group, a xylyl group, an indolyl group, a tetrahydronaphthyl group, a phenanthrenyl group, a biphenylenyl group, an indenyl group, an anthracenyl group, or a fluorenyl group. The aryl group may have a single ring, two fused rings, or three fused rings. In one embodiment, the aryl group may be a phenyl group.

n is an integer ranging from 1 to 1000 or from 2 to 1000.

Y is represented by anions, such as $HSO_4^-$, $CH_3SO_3^-$, $PhSO_3^-$, $p\text{-}tolSO_3^-$, or $CF_3SO_3^-$.

In the next step, the polysulfonium intermediate is demethylated to obtain a polyarylene sulfide.

The polysulfonium intermediate may be demethylated with aqueous HCl, HBr, or HI. In this regard, the acidity of the acid used for demethylation may be stronger than the acid used to obtain the polysulfonium intermediate.

The polysulfonium intermediate may be demethylated in an organic solvent. The organic solvent may be at least one selected from the group consisting of ketones, nitriles, sulfones, and amides. In one embodiment, the organic solvent may be a mixed solvent with water. In another embodiment, the organic solvent may be a mixed solvent of water and acetone.

The white polysulfonium solid may be dissolved in a mixed solvent (moderate ratio of water and organic solvent) and may be poured in hydrochloric acid slowly. The reaction keeps proceeding between 8 and 72 hours at room temperature, and a pale brown powdered product is obtained. In one embodiment, the reaction may proceed for 24 hours at room temperature wherein room temperature is defined as being about 18-25° C.

The disclosed embodiment is represented in the following reaction scheme:

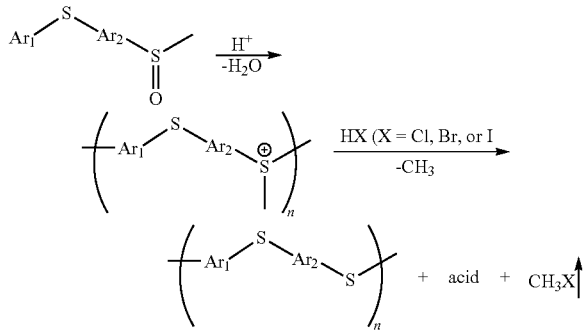

One example of a reaction scheme of the disclosed embodiment is shown below wherein a polysulfonium intermediate was obtained by reacting methyl 4-(phenylthio)phenyl sulfoxide with sulfuric acid and then demethylating the polysulfonium intermediate with aqueous hydrochloric acid to obtain a neutral PAS resin without salty waste as a byproduct.

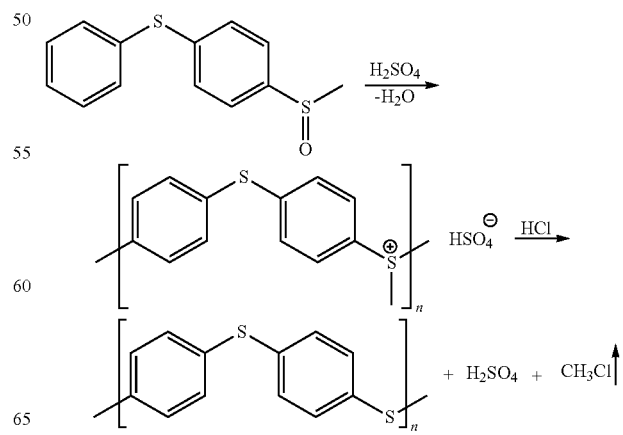

In this reaction scheme, aqueous hydrochloric acid is used as a nucleophile for demethylation of the polysulfonium intermediate to obtain the polyarylene sulfide (PAS) with a high yield and gaseous methyl chloride as byproduct.

As shown in the above reaction scheme, the sulfoxide group of the monomer is protonated to create a cationic hydroxysulfonium group, and π electrons of the aromatic rings are donated to create an electrophilic substitution reaction. Consequently, a soluble polycationic polymer with sulfonium groups is prepared. Aqueous HCl with a high dissociation constant is utilized as a nucleophile to remove the methyl groups on the sulfonium groups of the polycationic polymer, and a gaseous byproduct, $CH_3Cl$, is obtained without salty waste.

As shown in the reaction scheme of JP 07-304872 A, the salty waste may be a pyridinium salt. Other examples of a salty waste include alkali metal halides and alkaline-earth metal halides. The disclosed embodiment does not produce salty waste as a byproduct.

In contrast to conventional methods, the disclosed embodiment generates byproducts that may be at least one selected from the group consisting of sulfuric acid, methanesulfonic acid, trifluoromethanesulfonic acid, $CH_3Cl$, $CH_3Br$, and $CH_3I$. However, unlike conventional methods, the byproducts of the disclosed embodiment, $CH_3Cl$, $CH_3Br$, and $CH_3I$, are gases. As such, the method of the disclosed embodiment may not need further processing or purification steps since the byproducts, $CH_3Cl$, $CH_3Br$, and $CH_3I$, can be simply bubbled off. In this regard, the byproducts may also be collected for reuse. The byproducts, $CH_3Cl$, $CH_3Br$, and $CH_3I$, can be collected by traps in vacuum.

The disclosed embodiment will hereinafter be described with reference to exemplary embodiments, which are written to be understood only as examples and are not intended to limit the scope of the present application.

Examples

Synthesis of Polycationic Intermediate Shown in Scheme 1-1:

1 g (4 mmol) methyl-4-(phenylthio)phenyl sulfoxide was added into a 10 ml double-necked round-bottom flask with a stirrer, and 5 ml 97% sulfonic acid was dropped inside the reaction dropwise at 0° C. The reaction continued for about 1 hr at 0° C. Then, the temperature was raised to 25° C., and the reaction proceeded for 20 hr. After 20 hours, the reaction solution was poured in 200 ml ethanol, and a white precipitate (1.31 g, 100%) of a polysulfonium intermediate was obtained.

Synthesis of PPS Shown in Scheme 1-2:

The white precipitate (1.31 g) was dissolved in a mixed solvent (40 ml water and 20 ml acetone) and dropped in 50 ml 35% aqueous hydrochloric acid slowly. The reaction proceeded for 24 hr at room temperature, and a pale brown powdered product of PPS was obtained (0.8 g, 92%).

Scheme 1

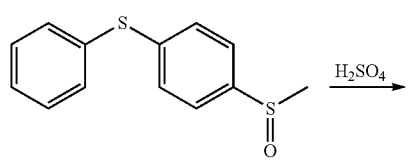

(1)

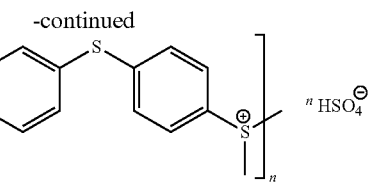

(2)

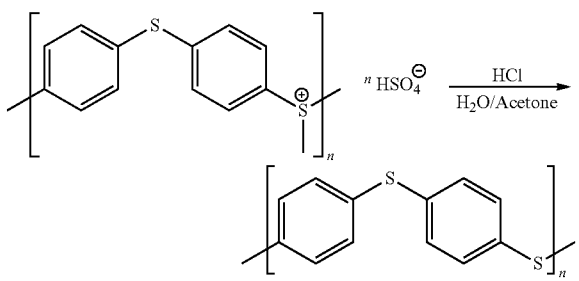

According to the DSC spectrum of FIG. 1, the melting point ($T_m$) of the PPS was between 267° C. and 280° C., and the crystallized point ($T_c$) was 211° C. In the IR spectrum of FIG. 2, the main absorption peaks were located at 3066, 1572, 1470, 1387, 809, 1091, 1093, and 1008 $cm^{-1}$.

It will be apparent to those skilled in the art that various modifications and variations can be made to the disclosed embodiments. It is intended that the specification and examples be considered as exemplary only with a true scope of the disclosure being indicated by the following claims and their equivalents.

The invention claimed is:

1. A method for preparing a polyarylene sulfide of formula (1), comprising:
reacting a methyl 4-(arylthio)aryl sulfoxide compound according to the following formula (2) with sulfuric acid, methanesulfonic acid, benzenesulfonic acid, p-toluenesulfonic acid, or trifluoromethanesulfonic acid to obtain a polysulfonium intermediate:

(1)

(2)

wherein $Ar_1$ and $Ar_2$ are aryl groups that are the same or different and n is an integer of 1 to 1000; and
demethylating the polysulfonium intermediate to obtain a polyarylene sulfide, wherein the polysulfonium intermediate is demethylated with aqueous HCl, HBr, or HI.

2. The method of claim 1, wherein the polyarylene sulfide is polyphenylene sulfide.

3. The method of claim 1, wherein the methyl 4-(arylthio)aryl sulfoxide compound is methyl 4-(phenylthio)phenyl sulfoxide.

4. The method of claim 1, wherein the polysulfonium intermediate is demethylated in an organic solvent.

5. The method of claim 4, wherein the organic solvent is at least one selected from the group consisting of ketones, nitriles, and amides.

6. The method of claim 1, wherein the method does not produce salty waste as a byproduct.

7. The method of claim 6, wherein the salty waste is a pyridinium salt.

8. The method of claim 1, wherein a purification step is not needed to prepare the polyarylene sulfide.

9. The method of claim 1, further comprising collecting byproducts for reuse.

10. The method of claim 9, wherein the byproducts are at least one selected from the group consisting of sulfuric acid, methanesulfonic acid, trifluoromethanesulfonic acid, $CH_3Cl$, $CH_3Br$, and $CH_3I$.

* * * * *